(12) United States Patent
Watanabe et al.

(10) Patent No.: US 9,700,691 B2
(45) Date of Patent: Jul. 11, 2017

(54) FLAVOR INHALATION PIPE

(75) Inventors: Tomoichi Watanabe, Tokyo (JP); Shinji Ishii, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 1098 days.

(21) Appl. No.: 13/592,430

(22) Filed: Aug. 23, 2012

(65) Prior Publication Data
US 2012/0318283 A1     Dec. 20, 2012

Related U.S. Application Data (63) Continuation of application No. PCT/JP2010/052835, filed on Feb. 24, 2010.

(51) Int. Cl.
*A61M 15/06* (2006.01)
*A24F 47/00* (2006.01)
*A61M 15/08* (2006.01)

(52) U.S. Cl.
CPC ........... *A61M 15/06* (2013.01); *A24F 47/002* (2013.01); *A61M 15/08* (2013.01)

(58) Field of Classification Search
None
See application file for complete search history.

(56) References Cited

U.S. PATENT DOCUMENTS

| | | | | |
|---|---|---|---|---|
| 2,119,198 A | * | 5/1938 | Bruder | A24F 1/28 131/181 |
| 2,124,221 A | * | 7/1938 | Jacobs | A24F 1/00 131/225 |
| 3,200,819 A | | 8/1965 | Gilbert | |
| 5,273,649 A | * | 12/1993 | Magnusson | C02F 1/002 210/232 |
| 5,535,735 A | | 7/1996 | McPherson | |
| 8,899,238 B2 | * | 12/2014 | Robinson | A24F 47/008 131/194 |
| 2008/0241255 A1 | | 10/2008 | Rose et al. | |

FOREIGN PATENT DOCUMENTS

| | | | | |
|---|---|---|---|---|
| CH | 698 603 B1 | 9/2009 | | |
| GB | 191218322 A | * | 0/1913 | ............... A24F 9/16 |
| JP | 50-013784 U | 2/1975 | | |
| JP | 53-9509 | 3/1978 | | |
| JP | 63-188039 U | 12/1988 | | |
| JP | H01-66898 U | 4/1989 | | |
| JP | 2-2331 A | 1/1990 | | |
| JP | 3-9678 Y2 | 3/1991 | | |
| JP | 2002-000331 A | 1/2002 | | |

\* cited by examiner

*Primary Examiner* — Michael J Felton
(74) *Attorney, Agent, or Firm* — Birch, Stewart, Kolasch & Birch, LLP (57) ABSTRACT

A flavor inhalation pipe includes a hollow cylindrical pipe body (10), a tobacco cartridge (12) accommodated, as a flavor generation cartridge, in the pipe body (10), a mouthpiece (30) coupled to the tobacco cartridge (12) and projecting from the pipe body (10), and a coupling device (40) coupling the pipe body (10) and the mouthpiece (30) to each other. The coupling device (40) has a coupling position in which the mouthpiece (30) is pressed against the pipe body (10) with a predetermined urging force to elastically coupled the two, and a release position which is assumed after the mouthpiece (30) in the coupling position is pushed into the pipe body (10) and then rotated and in which the coupling of the mouthpiece (30) to the pipe body (10) is released.

11 Claims, 7 Drawing Sheets

FLAVOR INHALATION PIPE

This application is a Bypass Continuation of PCT International Application No. PCT/JP2010/052835 filed on Feb. 24, 2010, which is hereby expressly incorporated by reference into the present application.

TECHNICAL FIELD

The present invention relates to a flavor inhalation pipe which allows a flavor emitted from a flavor generation source to be inhaled together with air.

BACKGROUND ART

This type of flavor inhalation pipe is disclosed, for example, in Patent Document 1. A smokeless tobacco product disclosed in Patent Document 1 includes a tubular pipe body, and the pipe body has a mouthpiece detachably inserted into one end thereof and a flavor generation cartridge accommodated therein. The flavor generation cartridge is filled therein with shredded tobacco, for example, and a desired flavoring is added to the shredded tobacco.

The user inhales through the mouthpiece of the smokeless tobacco product, whereupon he/she can have a pseudo feeling of smoking. Specifically, the interior of the flavor generation cartridge is filled with the flavors volatilized from the shredded tobacco and the flavoring, so that the user can enjoy the flavors by inhaling the air containing the flavors.

To facilitate the replacement of the flavor generation cartridge with a new one, a replacement device for a tobacco smoking pipe, disclosed in Patent Document 2, could be applied to the smokeless tobacco product of Patent Document 1. The replacement device includes a ring-like slider slidable on the outer peripheral surface of a pipe body in axial and circumferential directions of the pipe body, and engaging projections and engaging grooves detachably coupling the slider and a cartridge inside the pipe body to each other.

In this replacement device, as the slider is slid in an axial direction along the pipe body, an end portion of the cartridge is pulled out of the pipe body by the slider. With the cartridge thus pulled out, the slider is slid in a circumferential direction of the pipe body, whereby the engaging projections are disengaged from the engaging grooves. The slider is then returned to the original position, so that the end portion of the cartridge remains projecting from the pipe body and is exposed. The user can therefore hold the exposed end portion of the cartridge to detach the cartridge in its entirety from the pipe body.

The smokeless tobacco product of Patent Document 1 may be provided with a cap covering the mouthpiece. An example of such a cap is disclosed, for example, in Patent Document 3.

PRIOR ART LITERATURE

Patent Documents

Patent Document 1: Japanese Laid-open Patent Publication No. 02-2331.
Patent Document 2: Japanese Examined Utility Model Publication No. 53-9509
Patent Document 3: Japanese Laid-open Utility Model Publication No. 63-188039

DISCLOSURE OF THE INVENTION

Problems to be Solved by the Invention

Let it be assumed that the replacement device of Patent Document 2 is applied to the smokeless tobacco product of Patent Document 1. In this case, the flavor generation cartridge is in a free state when detached in its entirety from the pipe body. Thus, depending on the orientation of the pipe body, the flavor generation cartridge may drop into or slip out of the pipe body before the user holds the flavor generation cartridge, so that reliable and stable replacement of the flavor generation cartridge is not guaranteed.

Also, the coupling structure using the engaging projections and grooves is unable to completely eliminate the play of the flavor generation cartridge with respect to the slider, and thus the flavor generation cartridge cannot be stably held inside the pipe body.

Further, when pulling out the flavor generation cartridge, the user has to directly touch the flavor generation cartridge to hold same.

An object of the present invention is to provide a flavor inhalation pipe which enables a flavor generation cartridge to be stably held inside a pipe body, which permits the flavor generation cartridge to be pulled out of the pipe body without the need for the user to directly hold the flavor generation cartridge, and which can keep a mouthpiece hygienic during replacement of the flavor generation cartridge.

Means for Solving the Problems

The above object is achieved by a flavor inhalation pipe of the present invention, which comprises: a tubular pipe body having an open distal end and an open proximal end; a cylindrical flavor generation cartridge removably accommodated in the pipe body and filled therein with a flavor generation material from which flavor is volatilized, the flavor generation cartridge allowing air to flow from the distal end to the proximal end of the pipe body; a hollow mouthpiece detachably coupled to an end portion of the flavor generation cartridge located at the proximal end of the pipe body, the mouthpiece having a projecting portion projecting from the proximal end of the pipe body and a distal end portion located inside the pipe body; and a coupling device detachably coupling the proximal end of the pipe body and the distal end portion of the mouthpiece to each other, wherein the coupling device has a coupling position in which the pipe body and the mouthpiece are coupled to each other with the mouthpiece elastically pressed with a predetermined urging force against the pipe body in a push-out direction such that the distal end portion of the mouthpiece is pushed out of the proximal end of the pipe body, and a release position which is assumed after the mouthpiece is pushed into the pipe body against the urging force and then rotated relative to the pipe body and in which the distal end portion of the mouthpiece can be pulled off from the pipe body.

Preferably, the flavor inhalation pipe further comprises: a cap having an open end and configured to detachably cover the projecting portion of the mouthpiece; and an engaging device configured to engage the cap and the mouthpiece with each other in a circumferential direction of the cap when the cap is capped over the mouthpiece. Specifically, the engaging device includes a plurality of ribs protruding from an inner surface of the cap and configured to hold an end of the mouthpiece.

The coupling device, on the other hand, includes a flange formed on an outer peripheral surface of the mouthpiece, a circumferential groove formed in an inner peripheral surface of the proximal end of the pipe body and opening in the push-out direction at the proximal end, the circumferential groove providing, on the inner peripheral surface of the pipe body, a stepped surface facing the proximal end of the pipe body, an elastic member held between the flange and the stepped surface and configured to generate the urging force, a guide groove formed in the inner peripheral surface of the pipe body and opening in the stepped surface, the guide groove having an axial section extending from the stepped surface in an axial direction of the pipe body and a circumferential section extending from an end of the axial section in a circumferential direction of the pipe body, and an engaging lug formed on an outer peripheral surface of the distal end portion of the mouthpiece, wherein, when the engaging lug is located in the circumferential section of the guide groove and the urging force is exerted on the mouthpiece, the engaging lug comes into contact with a groove wall of the circumferential section of the guide groove to determine the coupling position.

Preferably, the elastic member is an elastic ring surrounding the outer peripheral surface of the mouthpiece. More specifically, an O ring may be used as the elastic member, and a cross-sectional shape of the O ring is not limited to circle.

In the above flavor inhalation pipe, when the coupling device is in the coupling position, the engaging lug of the mouthpiece is pressed against the groove wall of the circumferential section of the guide groove under the urging force of the elastic member. Accordingly, the mouthpiece is coupled to the pipe body in a stable manner.

Where the flavor inhalation pipe is provided with the cap, the user pulls the cap straight from the mouthpiece to have the mouthpiece exposed, before using the flavor inhalation pipe. Since, at this time, the coupling device is in the coupling position in which the mouthpiece is coupled to the pipe body, the mouthpiece is not pulled off together with the flavor generation cartridge from the pipe body.

The user can then put the exposed mouthpiece in his/her mouth and inhale through the mouthpiece. As a result of the inhalation, the flavor volatilized from the flavor generation material inside the flavor generation cartridge is guided, together with air, into the user's mouth cavity, so that the user can enjoy the flavor.

When the usage limit of the flavor generation cartridge is reached, the flavor generation cartridge needs to be replaced with a new one. In such case, the user holds the cap, or directly holds the mouthpiece, and then pushes the mouthpiece into the pipe body against the urging force. The push-in of the mouthpiece sets the engaging lug apart from the groove wall of the guide groove. Then, with the mouthpiece pushed in, the user rotates the mouthpiece in the circumferential direction of the pipe body, so that the engaging lug moves from the circumferential section to the axial section of the guide groove, changing the position of the coupling device from the coupling position to the release position. While the coupling device is in the release position, the user pulls the mouthpiece directly or indirectly via the cap in the push-out direction, whereupon the engaging lug moves along the axial section of the guide groove and comes out of the guide groove. That is, the mouthpiece is pulled out together with the flavor generation cartridge from the pipe body without being hindered by the engaging lug, so that the flavor generation cartridge is detached in its entirety from the pipe body.

The flavor generation cartridge thus pulled out is removed from the mouthpiece, and a new flavor generation cartridge is attached to the mouthpiece. Then, the user holds the mouthpiece directly or indirectly via the cap, and inserts the new flavor generation cartridge into the pipe body until the distal end portion of the mouthpiece is fitted into the pipe body. As the mouthpiece is inserted, the engaging lug moves along the axial section of the guide groove while compressing the elastic member, namely, the elastic ring or O ring, between the flange of the mouthpiece and the stepped surface of the pipe body, and as a result, the coupling device is located in the release position.

From the release position, the user rotates the mouthpiece in the circumferential direction of the pipe body, so that the engaging lug moves along the circumferential section of the guide groove. The user then stops pushing in the mouthpiece, whereupon the mouthpiece is acted upon by the urging force of the elastic ring or O ring and the engaging lug is brought into contact with the groove wall of the circumferential section of the guide groove. At this point, the coupling device is located in the coupling position and the replacement of flavor generation cartridges is completed.

Advantageous Effects of the Invention

In the flavor inhalation pipe according to the present invention, when the coupling device is in the coupling position, the mouthpiece is elastically coupled to the pipe body. Accordingly, the mouthpiece is not displaced with respect to the pipe body, thus ensuring stable coupling of the mouthpiece to the pipe body.

On the other hand, when the flavor generation cartridge is to be replaced, the user can pull out the flavor generation cartridge together with the mouthpiece from the pipe body while holding the mouthpiece, so that the flavor generation cartridge can be pulled out with ease. If the mouthpiece is covered with the cap at this time, the flavor generation cartridge can be replaced in a hygienic way since the user's thumb or fingers do not come into direct contact with the mouthpiece.

The other features and advantages of the present invention will become apparent from the following description of the best mode when taken in conjunction with the accompanying drawings.

BRIEF DESCRIPTION OF THE DRAWINGS

FIG. 6 illustrates a part of the flavor inhalation pipe of FIG. 2 in an enlarged manner, wherein FIG. 6(A) is an enlarged view of a part indicated by VI in FIG. 2, and FIG. 6(B) is a sectional view taken along line B-B in FIG. 6(A).

BEST MODE OF CARRYING OUT THE INVENTION

Figure 1:
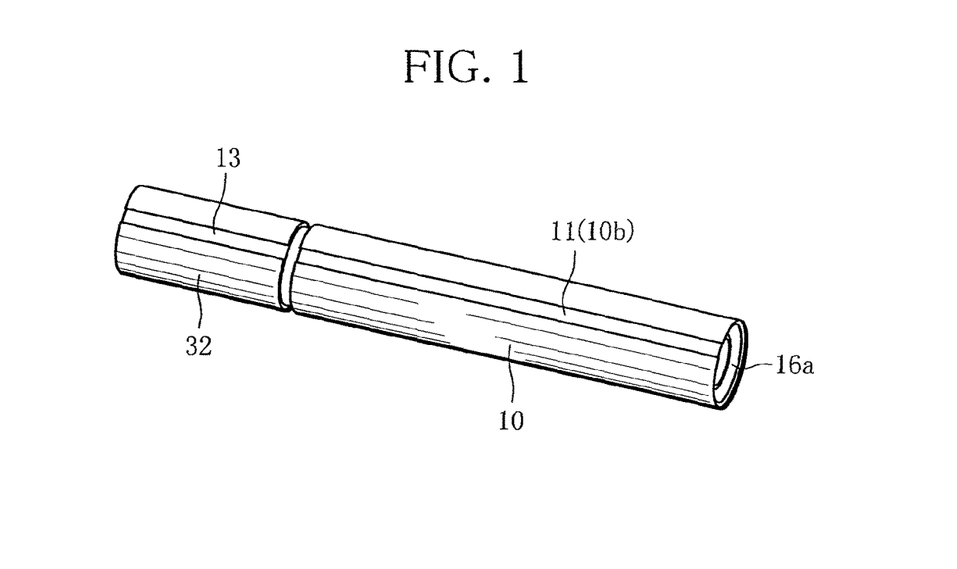
FIG. 1 is a perspective view of a flavor inhalation pipe according to one embodiment.
Figure 2:
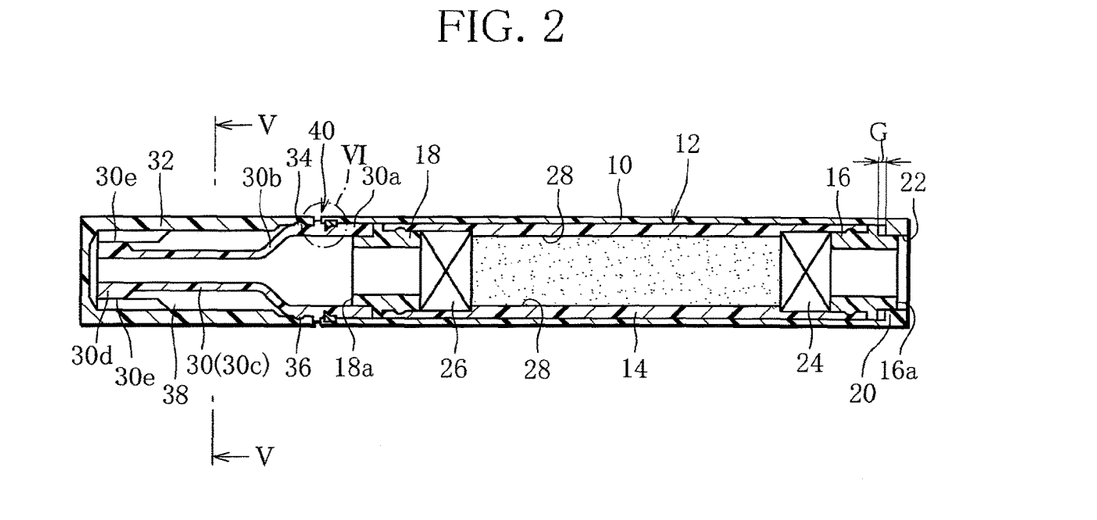
FIG. 2 is a longitudinal sectional view of the flavor inhalation pipe of FIG. 1.
Figure 3:
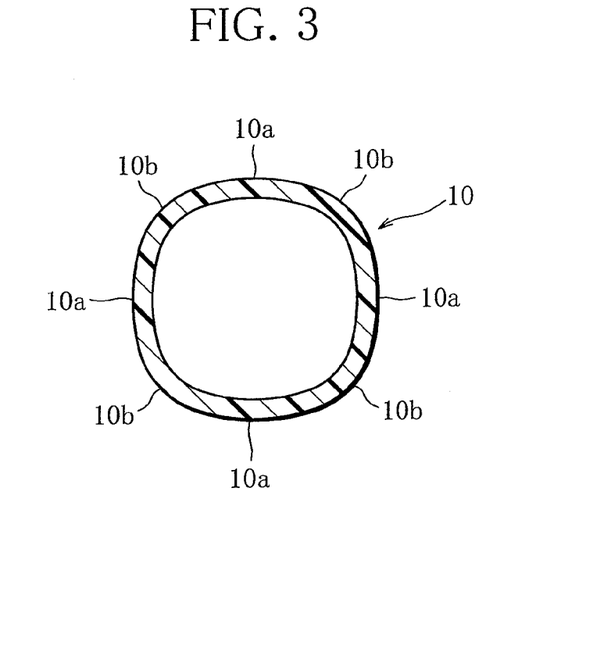
FIG. 3 is a cross-sectional view of a pipe body shown in FIG. 2.

Referring first to FIGS. 1 and 2, a flavor inhalation pipe according to one embodiment includes a tubular pipe body 10. The pipe body 10 is made of synthetic resin and is open at both ends. In this embodiment, the cross section of the pipe body 10 is not circular but resembles a square, as is clear from FIG. 3. Specifically, the cross section has a profile constituted by four large arcuate faces 10a, each resembling a flat face, and four small arcuate faces 10b connecting adjacent ones of the arcuate faces 10a and forming four stripes 11 on the outer peripheral surface of the pipe body 10, as shown in FIG. 1. The stripes 11 extend in an axial direction of the pipe body 10 and are arranged at intervals of 90° around the axis of the pipe body 10.

As illustrated in FIG. 2, a cylindrical tobacco cartridge 12 as a flavor generation cartridge is accommodated in the pipe body 10 coaxially therewith. The tobacco cartridge 12 is movable inside the pipe body 10 in axial and circumferential directions of the pipe body 10.

The tobacco cartridge 12 includes a tube 14, and end pieces 16 and 18 are fitted into opposite ends of the tube 14, respectively. The end pieces 16 and 18 are each in the form of a hollow sleeve and have projecting end portions 16a and 18a projecting from distal and proximal ends of the tube 14, respectively. Each of the projecting end portions 16a and 18a has a stepped shape, and has a flanged large-diameter section disposed in contact with a corresponding end face of the tube 14 and a small-diameter section extending from the large-diameter section. The large-diameter section has an outer diameter nearly equal to that of the tube 14, and the small-diameter section has an outer diameter smaller than that of the tube 14.

An annular protuberance 20 protrudes integrally from the inner peripheral surface at a distal end of the pipe body 10 and provides an insertion hole 22 at the distal end of the pipe body 10. The insertion hole 22 has an inner diameter slightly larger than the outer diameter of the small-diameter section of the projecting end portion 16a, and therefore, the small-diameter section of the projecting end portion 16a is removably inserted into the insertion hole 22, as illustrated in FIG. 2. It is to be noted here that a predetermined gap G is provided between the large-diameter section of the projecting end portion 16a and the annular protuberance 20.

The tube 14 and the end pieces 16 and 18 are each made of synthetic resin, and the tube 14 is preferably transparent or translucent.

Further, cylindrical filters 24 and 26 are arranged inside the tube 14 and adjoin the end pieces 16 and 18, respectively. The filters 24 and 26 each include a bundle of acetate fibers and a wrapper wrapping the bundle therein. The tube 14 has a filling chamber formed therein and between the filters 24 and 26, and the filling chamber is filled with tobacco material T at a predetermined density. The tobacco material T includes shredded tobacco and flavoring added to the shredded tobacco.

Figure 4:
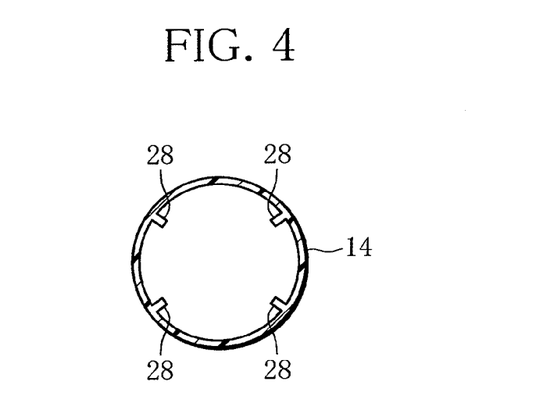
FIG. 4 is a cross-sectional view of a tube of a tobacco cartridge shown in FIG. 2.

The tube 14 has a plurality of ribs 28 formed integrally on its inner peripheral surface. The ribs 28 extend between the filters 24 and 26 in the axial direction of the tube 14 and, as clearly shown in FIG. 4, are arranged at intervals in the circumferential direction of the tube 14. The ribs 28 ensure required strength of the tube 14, contribute to reduction in wall thickness of the tube 14, and also serve as stoppers for the filters 24 and 26.

A predetermined distance is secured between the projecting end portion 18a of the end piece 18 and the proximal end of the pipe body 10, and a hollow mouthpiece 30 is detachably connected to the small-diameter section of the projecting end portion 18a.

Specifically, as is clear from FIG. 2, the hollow mouthpiece 30, which is made of synthetic resin, has a cylindrical large-diameter section 30a, a tapered section 30b and a flattened stem section 30c located in the mentioned order as viewed from the projecting end portion 18a of the end piece 18. The stem section 30c has a rectangular bulge 30d at its end, and the bulge 30d is larger in size than the stem section 30c and has a pair of flat surfaces 30e parallel with each other. The large-diameter section 30a of the mouthpiece 30 is removably inserted into the proximal end of the pipe body 10, and the small-diameter section of the projecting end portion 18a is detachably fitted into the large-diameter section 30a of the mouthpiece 30. Consequently, the flange of the end piece 18 is held between the large-diameter section 30a of the mouthpiece 30 and the tube 14. That is to say, the large-diameter section 30a of the mouthpiece 30 has an outer diameter slightly smaller than the inner diameter of the pipe body 10 and has an inner diameter slightly larger than the outer diameter of the small-diameter section of the projecting end portion 18a.

Part of the large-diameter section 30a, the tapered section 30b and the stem section 30c project from the proximal end of the pipe body 10, and the projecting portion of the mouthpiece 30 is covered with a cap 32 made of synthetic resin. The cap 32 is in the form of a hollow cylinder and has an open end and a closed end.

More specifically, the open end of the cap 32 has an inner diameter slightly larger than the outer diameter of the large-diameter section 30a of the mouthpiece 30. Thus, the cap 32 can receive, at its open end, the projecting portion of the mouthpiece 30 therein, and when the open end is fitted around the large-diameter section 30a, the cap 32 is detachably coupled to the mouthpiece 30.

The cap 32 has a cross section with a profile identical in size and shape to that of the aforementioned cross section of the pipe body 10. Accordingly, as shown in FIG. 1, the cap 32 has four stripes 13 formed on its outer peripheral surface and corresponding to the aforementioned stripes 11.

The open end of the cap 32 has a plurality of engaging recesses 34 formed in an inner surface thereof and arranged at regular intervals in the circumferential direction of the cap 32. On the other hand, the large-diameter section 30a of the mouthpiece 30 has engaging projections 36 formed on an outer peripheral surface thereof and associated with the respective engaging recesses 34. The engaging projections 36 also are arranged at regular intervals in the circumferential direction of the mouthpiece 30. Thus, the cap 32 is capped over the projecting portion of the mouthpiece 30, and when the engaging projections 36 are fitted in the respective engaging recesses 34, the cap 32 is detachably coupled to the mouthpiece 30. The engagement of the engaging projections 36 with the engaging recesses 34 prevents the cap 32 from undesirably coming off the mouthpiece 30 and also serves to make the user ensure that the mouthpiece 30 is normally covered with the cap 32.

Further, four ribs 38 are formed on an inner peripheral surface at the closed end of the cap 32. The ribs 38 extend in the axial direction of the cap 32 and are arranged at intervals in the circumferential direction of the cap 32.

Figure 5:
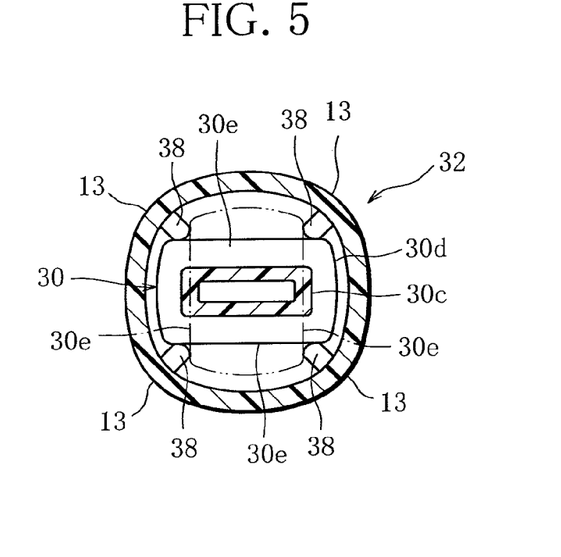
FIG. 5 is a sectional view taken along line V-V in FIG. 2.

Specifically, as illustrated in FIG. 5, when the cap 32 is normally capped over the mouthpiece 30, the four ribs 38 cooperatively hold the bulge 30d of the mouthpiece 30. More specifically, two ribs 38 come into contact with one flat surface 30e of the bulge 30d, and the remaining two ribs 38 come into contact with the other flat surface 30e of the bulge 30d. FIG. 5 also shows that the four ribs 38 are capable of holding the bulge 30d not only in a first orientation indicated by the solid line, but also in a second orientation indicated by the dot-dot-dash line, in which the bulge 30d, namely, the mouthpiece 30, is relatively rotated from the first orientation by 90°.

Holding the bulge 30d by the ribs 38 ensures, on one hand, that the cap 32 and the mouthpiece 30 are circumferentially coupled to each other irrespective of the orientation of the bulge 30d and, on the other hand, that the stripes 13 of the cap 32 and the corresponding stripes 11 of the pipe body 10 are aligned with each other, as will be clear from FIG. 1. That is, when the cap 32 is normally capped over the mouthpiece 30, the stripes 13 of the cap 32 are positioned with respect to the corresponding stripes 11 of the pipe body 10 in the circumferential direction of the pipe body 10 and the cap 32.

The large-diameter section 30a of the mouthpiece 30 is coupled not only to the end piece 18 of the tobacco cartridge 12 but also to the proximal end of the pipe body 10 by a coupling device 40 in a detachable manner.

Figure 6:
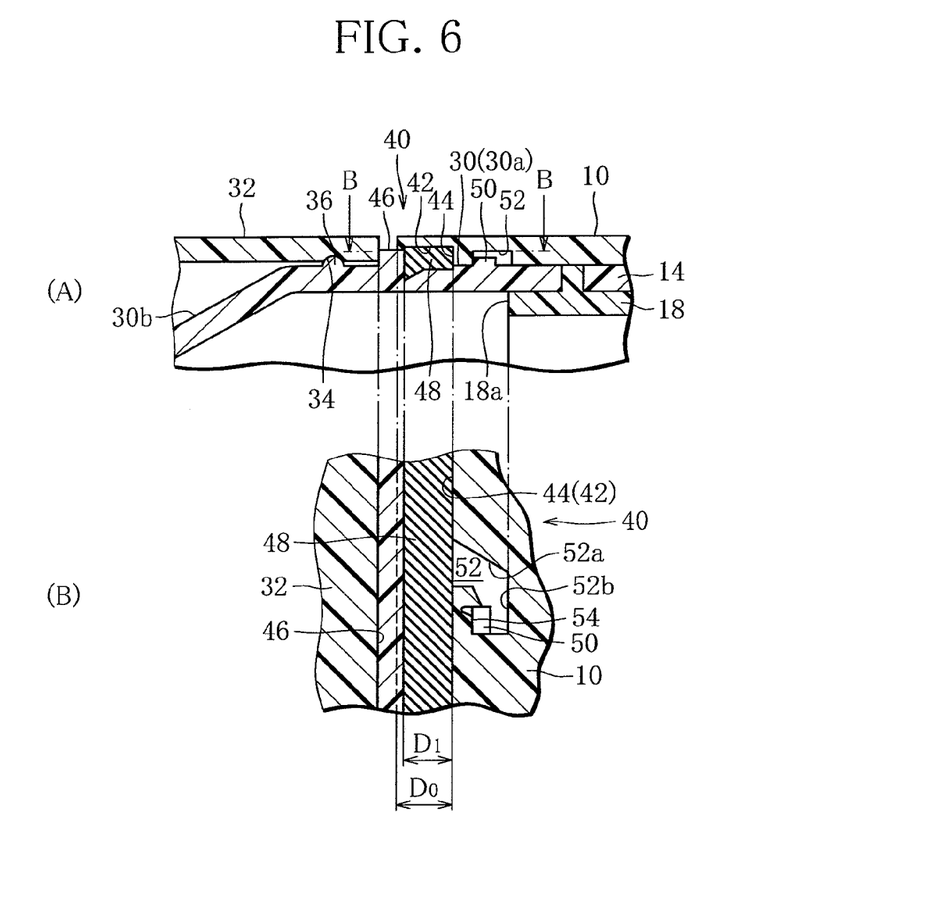
Figure 7:
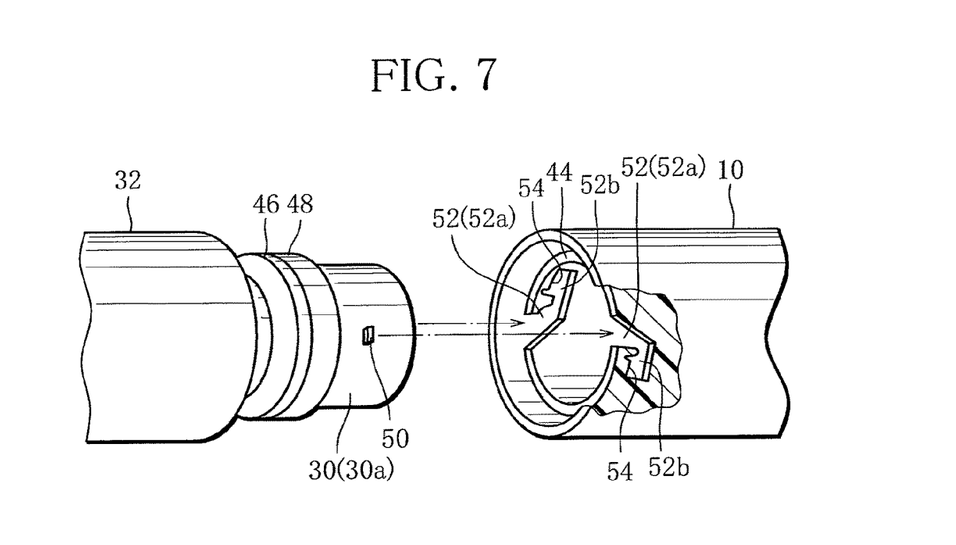
FIG. 7 is an exploded perspective view of a coupling device shown in FIG. 2.

The coupling device 40 is shown in detail in FIGS. 6 and 7. In the following, the coupling device 40 will be explained.

As illustrated in FIG. 6(A), the proximal end of the pipe body 10 has a circumferential groove 42 cut in an inner peripheral surface thereof. The circumferential groove 42 opens in the proximal end face of the pipe body 10 and also provides an annular stopper surface 44 on the inner peripheral surface of the pipe body 10.

On the other hand, the large-diameter section 30a of the mouthpiece 30 has a flange 46 formed integrally on its outer peripheral surface, and the flange 46 is located closer to the proximal end of the pipe body 10 than the aforementioned engaging projections 36 are. When the cap 32 is normally capped over the mouthpiece 30, the engaging projections 36 can be fitted in the respective engaging recesses 34 with the end face of the cap 32 brought into contact with the flange 46. That is, the flange 46 functions as a stopper for the cap 32 and determines the axial position of the cap 32 relative to the mouthpiece 30. It is to be noted that when the mouthpiece 30 is normally covered with the cap 32, a predetermined gap is secured between the inner surface of the closed end of the cap 32 and the corresponding end of the mouthpiece 30, as clearly shown in FIG. 2.

Also, the flange 46 has an outer diameter slightly smaller than the inner diameter of the circumferential groove 42, and therefore, as clearly shown in FIG. 6(A), the flange 46 partly enters the circumferential groove 42.

Further, an annular elastic member, or what is called an O ring 48, is fitted around the outer peripheral surface of the large-diameter section 30a of the mouthpiece 30. The O ring 48 is held between an end face of the flange 46 located opposite the engaging projections 36 and the stopper surface 44 of the circumferential groove 42. Specifically, the O ring 48 has an outer diameter smaller than the inner diameter of the circumferential groove 42 and, when in a free state, has a width $D_0$ identical with the width of the circumferential groove 42, for example. Accordingly, when the flange 46 partly enters the circumferential groove 42 as stated above, the O ring 48 is compressed between the flange 46 and the stopper surface 44 in the axial direction of the mouthpiece 30, and while in this state, the O ring 48 has a width $D_1$ smaller than the aforementioned width $D_0$, as clearly shown in FIG. 6(B).

While in the compressed state, the O ring 48 presses the mouthpiece 30 in a direction of detaching the mouthpiece 30 from the proximal end of the pipe body 10. Such detachment of the mouthpiece 30 is, however, prevented by engagement between the mouthpiece 30 and the pipe body 10.

Specifically, the large-diameter section 30a of the mouthpiece 30 has one or more, in this embodiment, two engaging lugs 50 formed on the outer peripheral surface thereof. The engaging lugs 50 are set apart from each other in a diametrical direction of the mouthpiece 30 and located closer to the distal end of the large-diameter section 30a than the O ring 48 is.

On the other hand, two guide grooves 52 are cut in the inner peripheral surface of the pipe body 10. The guide grooves 52 are set apart from each other in a diametrical direction of the pipe body 10 and receive the respective engaging lugs 50. Each guide groove 52 has a receiving seat facing the distal end of the pipe body 10, and the corresponding engaging lug 50 is pressed with a predetermined force against the receiving seat in urging contact therewith. The pressing force derives from the urging force exerted by the mouthpiece 30, namely, the restoring force of the compressed O ring 48.

Since the engaging lugs 50 are pressed against the receiving seats of the respective guide grooves 52 as stated above, the mouthpiece 30 is coupled reliably to the proximal end of the pipe body 10, so that the mouthpiece 30 does not come off the pipe body 10 together with the cap 32.

The shape of the guide grooves 52 will be now described in detail.

As is clear from FIGS. 6(B) and 7, each guide groove 52 has an axial section 52a extending in the axial direction of the pipe body 10 and opening in the stopper surface 44 of the circumferential groove 42, and a circumferential section 52b connected to an inner end of the axial section 52a. The circumferential section 52b extends from the inner end of the axial section 52a in the circumferential direction of the pipe body 10 by a predetermined length.

Out of the two groove walls forming the axial section 52a, at least the groove wall facing the end face of the circumferential section 52b is preferably not parallel with the axis of the pipe body 10 but inclined in a direction in which the circumferential section 52b extends.

Also, out of the two groove walls forming the circumferential section 52b, the groove wall located closer to the stopper surface 44 provides the aforementioned receiving seat. Specifically, this groove wall has a recess formed therein, and the recess forms, in cooperation with the end face of the circumferential section 52b, a recessed lug rest 54 allowing the engaging lug 50 to be fitted therein. Thus, while the engaging lug 50 is received in the lug rest 54 (while the coupling device 40 is in a coupling position), the lug rest 54 restricts the engaging lug 50 from three sides, whereby the engaging lug 50 is prevented from moving in such a direction that the engaging lug 50 is detached from the pipe body 10, as well as in the circumferential direction of the pipe body 10. As a result, the mouthpiece 30 is prevented from being displaced in both the axial and circumferential directions of the pipe body 10 at the same time.

Figure 8:
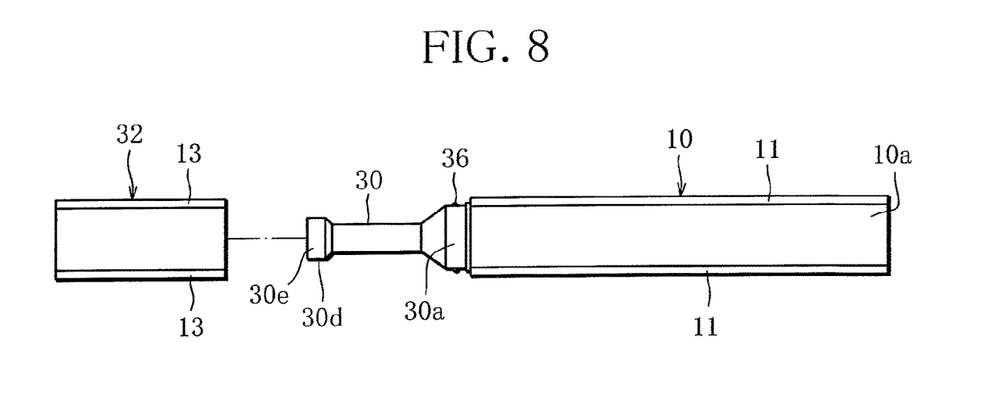
FIG. 8 illustrates the flavor inhalation pipe of FIG. 1 with a cap detached.

To use the flavor inhalation pipe of the aforementioned embodiment, first, the user pulls the cap 32 straight in the axial direction of the mouthpiece 30 to release the engagement between the engaging recesses 34 of the cap 32 and the engaging projections 36 of the mouthpiece 30. As the cap 32 is further pulled thereafter, the cap 32 is detached from the mouthpiece 30 as shown in FIG. 8, so that the mouthpiece 30 is exposed.

When the cap 32 is pulled off from the mouthpiece 30, the engaging lugs 50 of the mouthpiece 30 remain fitted in the lug rests 54 of the respective guide grooves 52, that is, the mouthpiece 30 is engaged with the pipe body 10. Thus, the mouthpiece 30 is not pulled off from the pipe body 10 together with the tobacco cartridge 12.

Then, with the bulge 30d of the mouthpiece 30 horizontally held in his/her mouth, the user inhales through the mouthpiece 30, whereupon he/she can enjoy the savor and taste characteristic of the shredded tobacco contained in the tobacco cartridge 12, as well as the flavor of the flavoring added to the shredded tobacco. Specifically, the interior of the tobacco cartridge 12 is filled with flavors volatilized from the shredded tobacco and the flavoring, and the user's inhalation creates a flow of air from the distal end of the pipe body 10 to the user's mouth cavity through the tobacco cartridge 12 and the mouthpiece 30. Accordingly, the flavors are guided together with the air flow into the user's mouth cavity, so that the user can enjoy the flavors without the need to light the shredded tobacco.

Also, when inhaling, the user holds the pipe body 10 with his/her index and middle fingers put on the similar, upper and lower arcuate faces 10a of the pipe body 10, and therefore, the pipe body 10 can be held in a stable manner.

Figure 9:
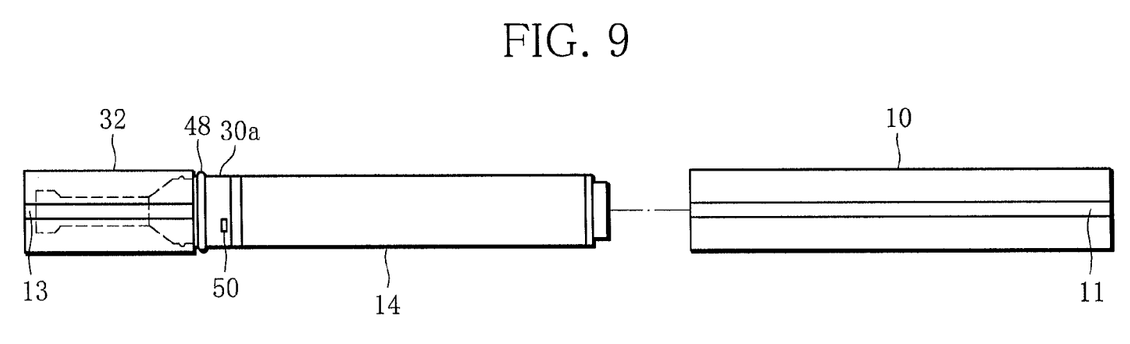
FIG. 9 illustrates a state in which the tobacco cartridge is pulled out, together with a mouthpiece, from the pipe body shown in FIG. 1.

On the other hand, when the usage limit of the tobacco cartridge 12 is reached, the user can detach the tobacco cartridge 12, together with the cap 32 and the mouthpiece 30, from the pipe body 10 as illustrated in FIG. 9.

Figure 10:
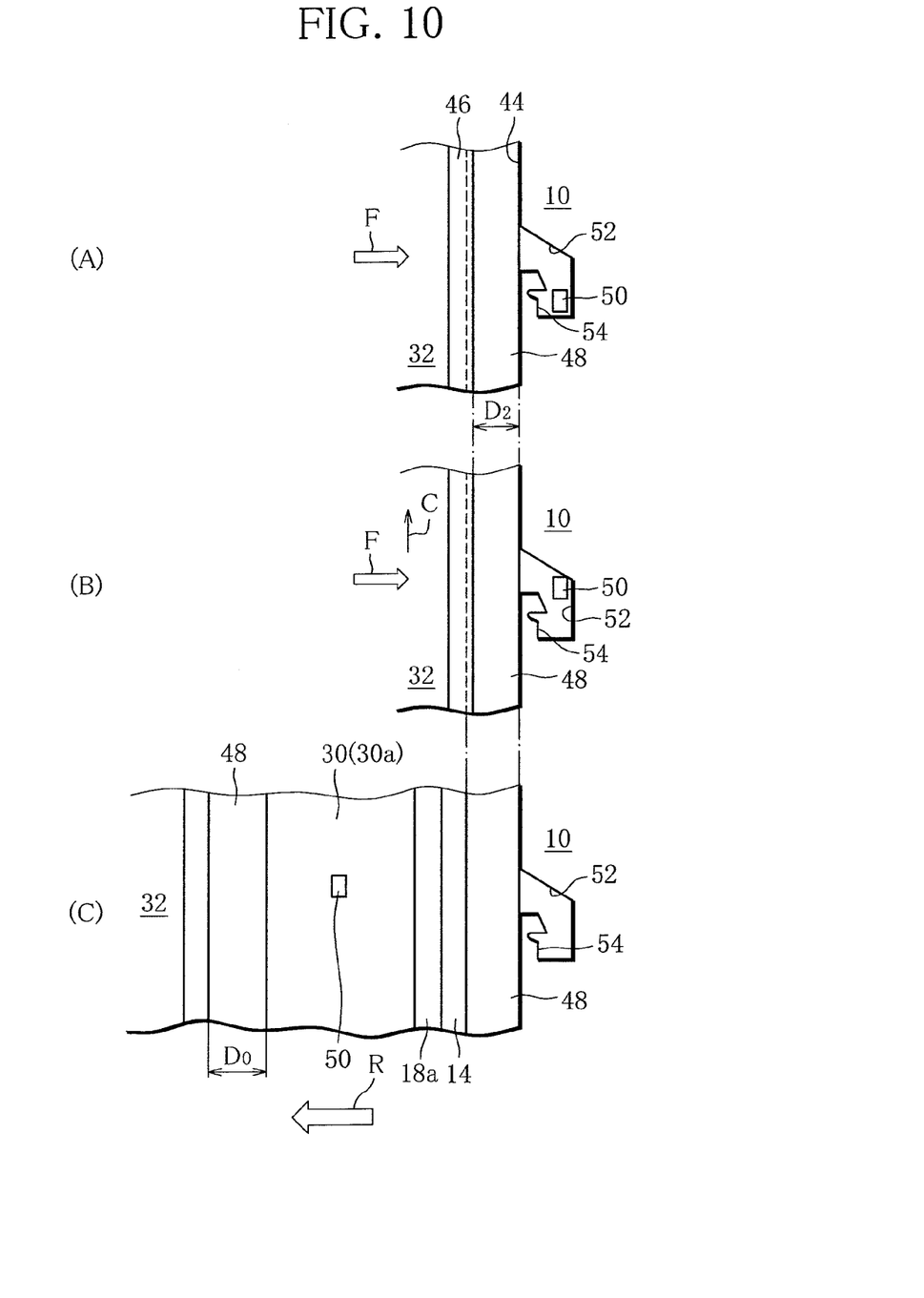
FIGS. 10(A) to 10(C) illustrate a procedure for pulling out the tobacco cartridge from the pipe body.

Referring now to FIG. 10, the manner of how the tobacco cartridge 12 is detached will be described in detail.

When the flavor inhalation pipe is in a non-use state as illustrated in FIG. 1, the user first pushes the cap 32 in a direction indicated by arrow F in FIG. 10(A), that is, toward the pipe body 10. At this time, the distal end of the cap 32 is in contact with the flange 46 of the mouthpiece 30 and also the distal end of the mouthpiece 30 is in contact with the flange of the end piece 18 of the tobacco cartridge 12. Accordingly, the push of the cap 32 causes the mouthpiece 30 and the tobacco cartridge 12 to move toward the distal end of the pipe body 10 in its axial direction. The tobacco cartridge 12 is allowed to move because the gap G (see FIG. 2) is provided between the flange of the end piece 16 of the tobacco cartridge 12 and the annular protuberance 20 of the pipe body 10, as stated above.

The above movement of the mouthpiece 30 disengages the engaging lugs 50 from the lug rests 54 of the respective guide grooves 52, as shown in FIG. 10(A), and also further compresses the O ring 48 between the flange 46 of the mouthpiece 30 and the stopper surface 44 of the pipe body 10, so that the width of the O ring 48 further reduces from $D_1$ to $D_2$.

Subsequently, with the cap 32 continuously pushed in, the user rotates the cap 32 about its axis in a direction indicated by arrow C in FIG. 10(B) (counterclockwise in FIG. 7). Since the cap 32 and the mouthpiece 30 are coupled to each other in the circumferential direction by the ribs 38 as mentioned above, the mouthpiece 30 and the tobacco cartridge 12 also rotate together with the cap 32. The rotation of the mouthpiece 30 causes each engaging lug 50 to move from the circumferential section 52b to the axial section 52a of the corresponding guide groove 52 (release position of the coupling device 40).

While in this state, the user stops pushing the cap 32, whereupon the mouthpiece 30 is pushed back in a push-out direction away from the pipe body 10 by the restoring force of the O ring 48 which has been compressed until then. Accordingly, the width of the O ring 48 returns from $D_2$ to $D_0$, and each engaging lug 50 moves along the axial section 52a toward the open end of the corresponding guide groove 52.

Then, the user holds the cap 32 and pulls the cap 32 back in a direction indicated by arrow R in FIG. 10(C), so that the engaging lugs 50 come out of the respective guide grooves 52, permitting the tobacco cartridge 12 to be pulled out of the pipe body 10 together with the mouthpiece 30. Consequently, the tobacco cartridge 12 can be detached with ease from the pipe body 10 as illustrated in FIG. 9.

Subsequently, the tobacco cartridge 12 is removed from the mouthpiece 30, and a new tobacco cartridge 12 is inserted at its end piece 18 into the mouthpiece 30, whereby the new tobacco cartridge 12 is coupled to the mouthpiece 30.

The user then holds the cap 32 and inserts the new tobacco cartridge 12 into the pipe body 10, and with the engaging lugs 50 of the mouthpiece 30 positioned with respect to the open ends of the respective guide grooves 52 of the pipe body 10 (see FIG. 7), the user pushes the large-diameter section 30a of the mouthpiece 30 into the proximal end of the pipe body 10 to cause the engaging lugs 50 to advance into the axial sections 52a of the respective guide grooves 52. Since, at this time, the O ring 48 of the mouthpiece 30 is held between the flange 46 of the mouthpiece 30 and the stopper surface 44 of the pipe body 10, the engaging lugs 50 move to the circumferential sections 52b of the respective guide grooves 52 (see FIG. 10(B)) while accompanying compression of the O ring 48.

Then, with the cap 32 and the mouthpiece 30 kept pushed in, the user rotates the cap 32 in the clockwise direction. Since the cap 32 is coupled to the mouthpiece 30 in the circumferential direction as mentioned above, the mouthpiece 30 and the tobacco cartridge 12 also rotate in the clockwise direction. Consequently, the engaging lugs 50 are brought into contact with the end faces of the respective circumferential sections 52b (see FIG. 10(A)), and while in this state, the user stops applying the pushing force to the cap 32 and the mouthpiece 30, whereupon the engaging lugs 50 are again fitted into the lug rests 54 of the respective guide grooves 52 as shown in FIG. 6(B). At this point, the replacement of the tobacco cartridges 12 is completed. Needless to say, the stripes 13 of the cap 32 are aligned with the respective stripes 11 of the pipe body 10 at this time.

The tobacco cartridge 12 may alternatively be replaced with a new one by first inserting a new tobacco cartridge 12 into the pipe body 10 and then pushing the mouthpiece 30 held by the cap 32 into the pipe body 10.

In connection with the replacement of the tobacco cartridges 12, since the user holds the mouthpiece 30 indirectly via the cap 32, his/her thumb or fingers do not come into direct contact with the mouthpiece 30. This permits the user to replace the tobacco cartridge 12 with a new one in a hygienic way.

The user can also replace the tobacco cartridge 12 with a new one without using the cap 32. In this case, the user directly holds the mouthpiece 30 and pushes and rotates the mouthpiece 30 in the aforementioned manner.

The tobacco cartridges 12 to be replaced is pulled out of the pipe body 10 together with the mouthpiece 30 regardless of whether the cap 32 is used or not, thus enabling reliable and easy detachment of the tobacco cartridge 12 from the pipe body 10. Also, a situation where the detached tobacco cartridge 12 undesirably drops off from the pipe body 10 does not arise.

While the flavor inhalation pipe according to the embodiment has been described above, the present invention is not limited to the foregoing embodiment and may be modified in various ways.

For example, the flavor inhalation pipe may use, in place of the tobacco cartridge 12, a flavor generation cartridge containing a variety of flavor generation materials. In this case, the user can enjoy flavors emitted from the flavor generation materials.

Also, the pipe body 10 and the cap 32 may bear, on their outer peripheral surfaces, respective divided portions of a continuous pattern or design, in place of the aforementioned stripes 11 and 13. In this case, when the cap 32 is capped over the mouthpiece 30, the pattern or design portion of the pipe body 10 and that of the cap 32 are positioned with respect to each other to form the continuous pattern or design.

Further, the coupling device 40 may use an elastic member such as a compression coil spring, in place of the O ring 48. Also, the configurations of the tobacco cartridge, mouthpiece, cap and the like may be modified as desired on condition that the function of the coupling device 40 is not affected.

EXPLANATION OF REFERENCE SIGNS

10 pipe body
12 tobacco cartridge
30 mouthpiece
30a large-diameter section (distal end portion)
32 cap
40 coupling device
42 circumferential groove
44 stopper surface (stepped surface)
46 flange
48 O ring (elastic member)
50 engaging lug
52 guide groove
52a axial section
52b circumferential section
54 lug rest
11, 13 stripe (pattern)

The invention claimed is:

1. A flavor inhalation pipe comprising:
  a tubular pipe body having an open distal end and an open proximal end;
  a flavor generation cartridge removably accommodated in said pipe body and including a tube provided with end pieces fitted into opposite ends of the tube and in the form of hollow sleeves, the tube being filled therein with a flavor generation material from which flavor is volatilized, said flavor generation cartridge allowing air to flow from the distal end to the proximal end of said pipe body;
  a hollow mouthpiece detachably coupled to an end portion of the tube located at the proximal end of said pipe body, said mouthpiece having a projecting portion projecting from the proximal end of said pipe body and a distal end portion located inside said pipe body;
  a cap having an open end and configured to detachably cover the projecting portion of said mouthpiece;
  an engaging device configured to engage said cap and said mouthpiece with each other in a circumferential direction of said cap when said cap is capped over said mouthpiece; and
  a coupling device detachably coupling the proximal end of said pipe body and the distal end portion of said mouthpiece to each other, said coupling device having a coupling position in which said pipe body and said mouthpiece are coupled to each other with said mouthpiece elastically pressed with a predetermined urging force against said pipe body in a push-out direction such that the distal end portion of said mouthpiece is pushed out of the proximal end of said pipe body, and a release position which is assumed after said mouthpiece is pushed into said pipe body via the cap against the urging force with the cap and the mouthpiece engaged with each other by the engaging device and then rotated via the cap relative to said pipe body and in which the distal end portion of said mouthpiece can be pulled off together with said flavor generation cartridge from said pipe when the cap is detached.

2. The flavor inhalation pipe according to claim 1, wherein said engaging device includes a plurality of ribs protruding from an inner surface of said cap and configured to hold an end of said mouthpiece.

3. The flavor inhalation pipe according to claim 2, wherein said pipe body and said cap bear, on outer peripheral surfaces thereof, respective divided portions of a continuous pattern, and when said cap is capped over said mouthpiece with the end of said mouthpiece held by the ribs, the respective divided portions of the pattern on said pipe body and said cap are circumferentially positioned with respect to each other to form the continuous pattern.

4. The flavor inhalation pipe according to claim 1, wherein said coupling device includes
  a flange formed on an outer peripheral surface of said mouthpiece,
  a circumferential groove formed in an inner peripheral surface of the proximal end of said pipe body and opening in the push-out direction at the proximal end, the circumferential groove providing, on the inner peripheral surface of said pipe body, a stepped surface facing the proximal end of said pipe body,
  an elastic member held between the flange and the stepped surface and configured to generate the urging force,
  a guide groove formed in the inner peripheral surface of said pipe body and opening in the stepped surface, the guide groove having an axial section extending from the stepped surface in an axial direction of said pipe body, and a circumferential section extending from an end of the axial section in a circumferential direction of said pipe body, and
  an engaging lug formed on an outer peripheral surface of the distal end portion of said mouthpiece, wherein, when the engaging lug is located in the circumferential section of the guide groove and the urging force is exerted on said mouthpiece, the engaging lug comes into contact with a groove wall of the circumferential section of the guide groove to determine the coupling position.

5. The flavor inhalation pipe according to claim 4, wherein the elastic member is an elastic ring surrounding the outer peripheral surface of said mouthpiece.

6. The flavor inhalation pipe according to claim 5, wherein the elastic ring is an O ring.

7. The flavor inhalation pipe according to claim 4, wherein the flange has an outer diameter slightly smaller than an inner diameter of the circumferential groove of said pipe body, and when said coupling device is in the coupling position, the flange partly enters the circumferential groove.

8. The flavor inhalation pipe according to claim 4, wherein said coupling device further includes a recessed lug rest formed in the groove wall of the circumferential section of the guide groove and configured to receive the engaging lug when said coupling device in the coupling position, the lug rest restricting the engaging lug not only in the push-out direction but also in the circumferential direction of said pipe body.

9. The flavor inhalation pipe according to claim 4, further comprising:
- a cap having an open end and configured to detachably cover the projecting portion of said mouthpiece; and
- an engaging device configured to engage said cap and said mouthpiece with each other in a circumferential direction of said cap as well as in a push-in direction of said mouthpiece when said cap is capped over said mouthpiece.

10. The flavor inhalation pipe according to claim 9, wherein, when said cap is capped over the projecting portion of said mouthpiece, said cap and the elastic member cooperatively hold the flange therebetween.

11. The flavor inhalation pipe according to claim 1, wherein the flavor generation material includes a tobacco material.

* * * * *